United States Patent
Ryder et al.

(10) Patent No.: US 8,852,223 B2
(45) Date of Patent: Oct. 7, 2014

(54) FIXED WIRE DILATATION CATHETER WITH AN ELONGATEABLE DISTAL END

(75) Inventors: John Kenneth Ryder, Coral Springs, FL (US); John Schreiner, Weston, FL (US)

(73) Assignee: Cordis Corporation, Miami Lakes, FL (US)

( * ) Notice: Subject to any disclaimer, the term of this patent is extended or adjusted under 35 U.S.C. 154(b) by 2191 days.

(21) Appl. No.: 11/697,538

(22) Filed: Apr. 6, 2007

(65) Prior Publication Data
US 2008/0249465 A1    Oct. 9, 2008

(51) Int. Cl.
*A61M 29/00* (2006.01)
*A61M 31/00* (2006.01)
*A61M 25/10* (2013.01)
*A61M 25/01* (2006.01)

(52) U.S. Cl.
CPC ..... *A61M 25/104* (2013.01); *A61M 2025/1093* (2013.01); *A61M 2025/0186* (2013.01)
USPC .......................................... 606/194; 604/509

(58) Field of Classification Search
USPC ............................. 604/103.09, 509; 606/194
See application file for complete search history.

(56) References Cited

U.S. PATENT DOCUMENTS

| | | | | |
|---|---|---|---|---|
| 3,773,034 A | * | 11/1973 | Burns et al. .................... | 600/434 |
| 4,719,924 A | * | 1/1988 | Crittenden et al. ............ | 600/585 |
| 4,748,986 A | * | 6/1988 | Morrison et al. .............. | 600/585 |
| 4,757,827 A | * | 7/1988 | Buchbinder et al. .......... | 600/585 |
| 4,771,778 A | * | 9/1988 | Mar .............................. | 606/192 |
| 4,886,067 A | * | 12/1989 | Palermo ......................... | 600/434 |
| 4,917,102 A | * | 4/1990 | Miller et al. .................. | 600/585 |
| 4,940,062 A | * | 7/1990 | Hampton et al. ............. | 600/585 |
| 4,964,409 A | * | 10/1990 | Tremulis ....................... | 600/434 |
| 4,998,917 A | * | 3/1991 | Gaiser et al. ............. | 604/103.13 |
| 5,135,503 A | * | 8/1992 | Abrams .................... | 604/164.13 |
| 5,290,230 A | * | 3/1994 | Ainsworth et al. ...... | 604/103.09 |
| 5,345,945 A | * | 9/1994 | Hodgson et al. ............. | 600/585 |
| 5,397,305 A | * | 3/1995 | Kawula et al. ............ | 604/96.01 |
| 5,411,476 A | * | 5/1995 | Abrams et al. ............ | 604/95.01 |
| 5,451,209 A | * | 9/1995 | Ainsworth et al. ...... | 604/103.09 |
| 5,520,645 A | * | 5/1996 | Imran et al. .................. | 606/194 |
| 5,545,200 A | * | 8/1996 | West et al. ................... | 607/122 |
| 5,571,169 A | * | 11/1996 | Plaia et al. ................... | 128/898 |
| 5,636,642 A | * | 6/1997 | Palermo ........................ | 600/585 |
| 5,728,133 A | * | 3/1998 | Kontos ......................... | 606/213 |
| 5,749,837 A | * | 5/1998 | Palermo et al. .............. | 600/585 |
| 5,755,760 A | * | 5/1998 | Maguire et al. .............. | 607/122 |
| 5,882,333 A | * | 3/1999 | Schaer et al. ............. | 604/95.01 |
| 5,908,405 A | * | 6/1999 | Imran et al. .................. | 604/508 |
| 6,139,510 A | * | 10/2000 | Palermo ........................ | 600/585 |
| 6,146,339 A | * | 11/2000 | Biagtan et al. ............... | 600/585 |
| 6,355,016 B1 | * | 3/2002 | Bagaoisan et al. ....... | 604/103.09 |

(Continued)

OTHER PUBLICATIONS

Cordis STEER-IT™ Deflecting Tip Guidewire brochure—Jun. 2005.

(Continued)

*Primary Examiner* — Katherine Dowe
*Assistant Examiner* — Michael Mendoza
(74) *Attorney, Agent, or Firm* — Cook Alex Ltd.

(57) ABSTRACT

A fixed wire dilatation catheter for treating the vasculature of a patient. The dilatation catheter includes an elongated member that has a distal end portion which can be elongated to puncture through blockages within the blood vessels. The dilatation catheter also includes an expandable device located along the elongated member at a location proximal the distal end portion of the elongated member.

18 Claims, 2 Drawing Sheets

(56) References Cited

U.S. PATENT DOCUMENTS

| | | |
|---|---|---|
| 6,402,720 B1 | 6/2002 | Miller et al. |
| 6,569,148 B2 * | 5/2003 | Bagaoisan et al. ............ 604/509 |
| 6,575,920 B2 * | 6/2003 | Zhou ............................ 600/585 |
| 6,585,718 B2 * | 7/2003 | Hayzelden et al. ........... 604/523 |
| 6,638,222 B2 | 10/2003 | Chandrasekaran et al. |
| 6,669,670 B1 * | 12/2003 | Muni et al. ............... 604/164.13 |
| 6,716,183 B2 * | 4/2004 | Clayman et al. ............. 600/585 |
| 7,044,921 B2 * | 5/2006 | Asmus et al. ................. 600/585 |
| 7,128,718 B2 * | 10/2006 | Hojeibane et al. ........... 600/585 |
| 7,160,266 B2 | 1/2007 | Shkolnik |
| 7,166,100 B2 | 1/2007 | Jordan et al. |
| 7,182,735 B2 * | 2/2007 | Shireman et al. ............. 600/585 |
| 7,351,214 B2 * | 4/2008 | Burgermeister .............. 600/585 |
| 7,481,778 B2 * | 1/2009 | Cedro et al. .................. 600/585 |
| 7,520,863 B2 * | 4/2009 | Grewe et al. .................. 600/585 |
| 7,771,388 B2 * | 8/2010 | Olsen et al. ................. 604/95.04 |
| 2002/0026145 A1 * | 2/2002 | Bagaoisan et al. ......... 604/96.01 |
| 2004/0082881 A1 * | 4/2004 | Grewe et al. .................. 600/585 |
| 2007/0083253 A1 | 4/2007 | Fischell et al. |

OTHER PUBLICATIONS

Cordis STEER-IT® Deflecting Tip Guidewire website printouts—circa 2002.

* cited by examiner

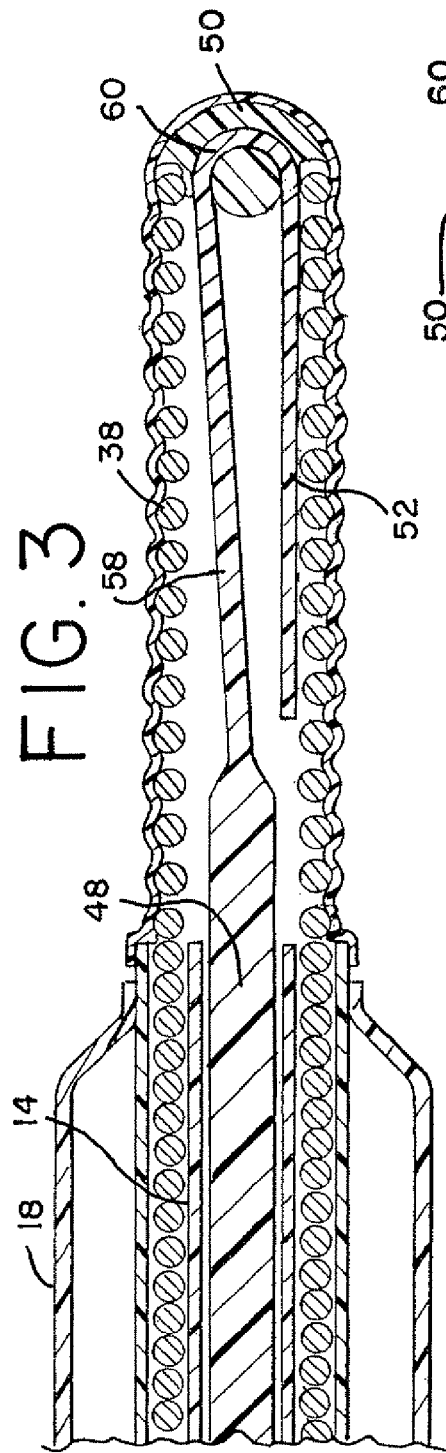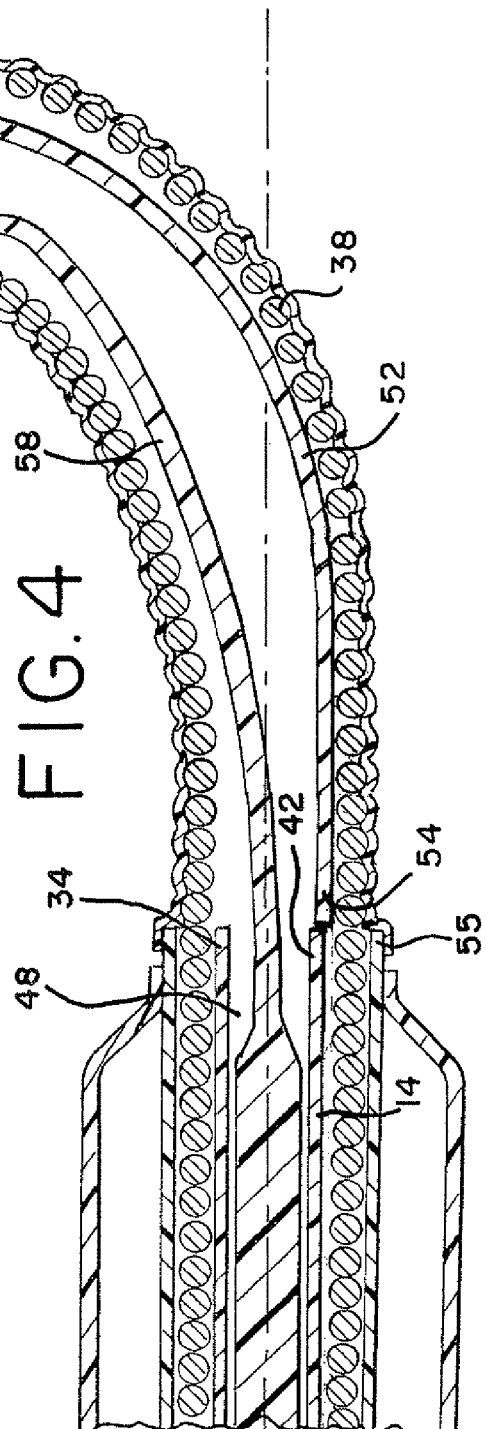

FIXED WIRE DILATATION CATHETER WITH AN ELONGATEABLE DISTAL END

FIELD OF THE INVENTION

The present invention is related to dilatation catheters, and more particularly to fixed wire dilatation catheters having an elongateable distal end.

BACKGROUND OF THE INVENTION

One type of vascular disease is occlusive vascular disease, which includes conditions sometimes referred to as chronic total occlusion (CTO). A typical CTO is a lesion located in a blood vessel of a patient that results from an accumulation of deposits, typically calcified fibrin, therein. Occlusive vascular disease can cause blockages in both coronary and peripheral blood vessels. A blockage in a coronary blood vessel is a very serious condition that can lead to angina or myocardial infarction.

Occlusive vascular disease is generally characterized by a hardened, calcified deposit substantially or completely blocking the flow of blood through a blood vessel. Traditionally, this type of disease has been treated by both bypass surgery and/or drug therapy. Recently, it has been discovered that occlusive vascular disease can also be treated by advancing a guidewire through or across the diseased location to create a passageway for interventional treatment, i.e. angioplasty. In such a procedure, the guidewire is used to puncture through the hard deposit in order to create a pathway for balloon catheter or stent delivery to the lesion site. Techniques in this regard can include what is known in the art as "dottering" by which the device is subjected to short alternating advancing and retrograde movement so the tip or the like that engages the lesion site imparts short thrusts to in a sense peck away at the diseased location.

Typically, a guidewire and a catheter are separate devices that are used in percutaneous transluminal coronary angioplasty (PTCA) procedures, with the guidewire performing essentially a guiding function for the PTCA catheter that effects the desired medical procedure. The present disclosure recognizes that combining a guidewire-type device with a PTCA catheter into an integral device can have important advantages.

Some of the challenges that have been encountered in using the guidewire technique for occlusive vascular disease treatment include difficulty in positioning the guidewire prior to and during the lesion crossing procedure and misalignment of the distal tip of the guidewire, which has the potential to lead to unintended perforation of the blood vessel.

Therefore, a need remains for a medical device that can be easily positioned prior to and during lesion crossing and/or treatment and also reduces the risk of perforating the blood vessel.

SUMMARY OF INVENTION

The present invention embodies medical devices and methods that have application in treating diseases of the vasculature of a patient, with particular application for treating occlusive vascular disease. Although the medical devices and methods disclosed herein have application in treating blood vessels, the medical devices and methods are not intended to be limited to such use and may be used to treat other areas of the human body.

The invention generally includes a fixed wire dilatation catheter that includes a deflectable distal end portion for guiding the catheter through the tortuous pathways of the vascular system. The distal end portion can also be elongated in a longitudinal direction for contacting and/or advancement through a lesion site.

One aspect of the present invention is generally related to a steerable dilatation catheter that includes an outer flexible tubular member and an inner flexible tubular member disposed therein. One or both of the outer and inner flexible tubular members can be comprised of any suitable type of a tubular flexible member having the strength and flexibility for traversing the vasculature of a patient.

The outer flexible tubular member has an expandable member near the distal end thereof. The expandable member is any suitable type of expandable member and could be, for example, a polyamide medical balloon device that is inflatable, such as a nylon inflatable balloon. The inner flexible tubular member has a proximal end portion, a distal end portion and a lumen disposed therein. The distal end portion of the inner flexible tubular member, which typically forms a portion of the distal end of the dilatation catheter, extends distally beyond the distal end of the outer flexible tubular member. Additionally, the distal end of the outer flexible tubular member is secured to the inner flexible tubular member.

The dilatation catheter also includes an elongated deflection member that has a proximal end portion and a distal end portion. The deflection member is slidably disposed within the lumen of the inner flexible tubular member and the distal end portion of the deflection member is operatively connected to the distal end portion of the inner tubular member. Furthermore, the dilatation catheter also includes a retaining member that has a proximal end portion and a distal end portion. The distal end portion of the retaining member is operatively connected to the distal end portion of the inner tubular member and the proximal end portion of the retaining member includes a free end which is slidably movable within the inner tubular member. During the operation of the dilatation catheter, the distal end portion of the inner tubular member can be extended or elongated in the distal direction by movement of the deflection member in a longitudinal direction.

Another aspect of the present invention generally relates to a steerable dilatation catheter for treating a TCO within the vasculature of a patient. The dilatation catheter comprises an elongated member having a deflectable distal end portion for guiding the elongated member through the vasculature of a patient to a site of a TCO. The distal end portion of the elongated member is also extendable in a substantially axial direction for treating the TCO. The dilatation catheter also includes an expandable member located along the elongated member.

Yet a further aspect of the present invention generally relates to a steerable dilatation catheter having a deflectable and extendable or elongateable distal tip. The dilatation catheter comprises an outer flexible tubular member and an inner flexible tubular member. Both the outer and inner flexible tubular members can be any suitable type of flexible tubular members for traversing the vascular of a patient, such as a hypotube having the strength and flexibility to be advanced through the vasculature of a patient.

The outer flexible tubular member includes an inflatable medical device, such as an inflatable medical balloon at or near the distal end thereof. The inner flexible tubular member has a proximal end portion, a distal end portion and an inner lumen therethrough. The distal end portion of the inner tubular member is comprised of a flexible member, such as a flexible helical coil. Additionally, the distal end portion of the inner flexible tubular member, which typically comprises a portion of the distal end of the dilatation catheter, extends distally beyond the distal end of the outer flexible tubular member.

The dilatation catheter also includes a passageway defined between the outer tubular member and the inner tubular member which is in fluid communication with the inflatable member. The passageway can be used to infuse fluid, typically saline, into the inflatable member for inflation thereof.

Furthermore, the dilatation catheter also includes an elongated deflection member and a retaining member disposed within the inner lumen of the inner tubular member. The deflection member includes a proximal end portion and a distal end portion wherein the distal end portion of the elongated deflection member is operatively connected to the distal end portion of the inner tubular member. The retaining member has a proximal end portion and a distal end portion. The distal end portion of the retaining member is operatively connected to the distal end portion of the inner tubular member and the proximal end portion of the retaining member includes a free end that is adapted to engage the inner tubular member when the elongated deflection member is moved in a proximal direction.

During operation of the dilatation catheter, the distal end portion of the inner tubular member can be deflected by moving the deflection member longitudinally in the proximal direction. The distal end portion of the dilation catheter can also be extended or elongated by moving the deflection member longitudinally in the distal direction.

Another aspect of the present invention generally relates to a method of treating a occlusive vascular disease of a blood vessel. The method generally comprises advancing a distal end portion of an elongated member, such as the distal end portion of a fixed wire dilatation catheter, through the vasculature of a patient to the diseased site. Then one can distally extend or elongate the distal end portion of the elongated member to treat the diseased site, by for example, extending the distal end portion so as to advance the distal end portion through or across the site or by contacting the site in a pecking or drill-like action.

Other aspects, objects and advantages of the present invention will be understood from the following description according to the preferred embodiments of the present invention, specifically including stated and unstated combinations of the various features which are described herein, relevant information concerning which is shown in the accompanying drawings.

BRIEF DESCRIPTION OF THE DRAWINGS

In describing the preferred embodiments of the present invention, reference will be made to the accompanying drawings, wherein:

FIG. 3 is an enlarged cross-sectional view of the distal end portion of the fixed wire dilatation catheter of FIG. 1 shown in an elongated configuration; and FIG. 4 is an enlarged cross-sectional view of the distal end portion of the fixed wire dilatation catheter of FIG. 1 shown deflected from its normal position.

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

Figure 1:
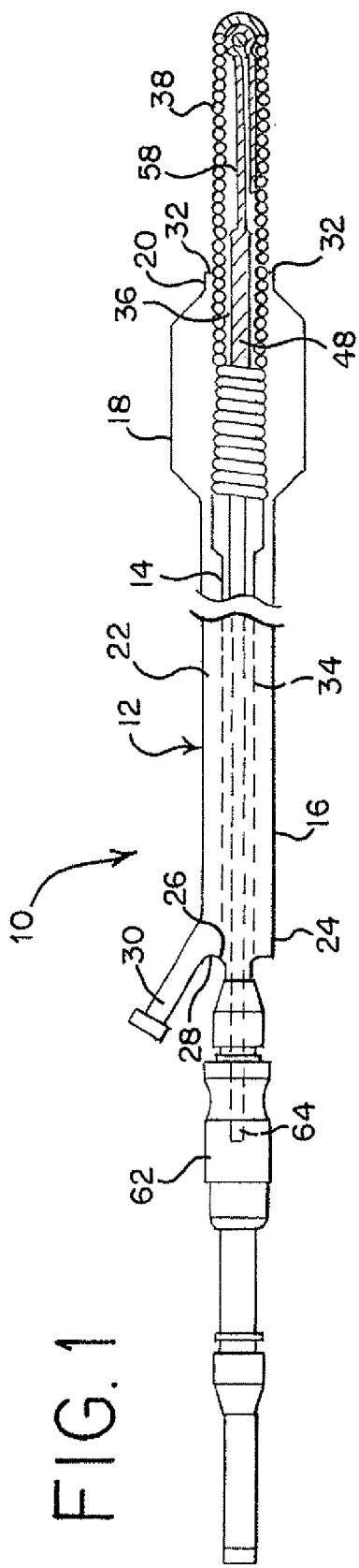
FIG. 1 is a longitudinal side elevational view, partially in cross-section, of one embodiment of a fixed wire dilatation catheter of the present invention.

FIG. 1 generally illustrates a particular embodiment of a fixed wire dilatation catheter of the present invention, generally designated as 10. The dilatation catheter 10 includes an elongated outer tubular member, generally designated at 12, and an elongated inner tubular member 14 disposed within the outer tubular member 12. The outer tubular member 12 includes an elongated shaft 16, preferably a hypotube, and an expandable member 18, located at or near the distal end portion 20 of the outer tubular member 12.

The expandable member 18 can be any suitable type of expandable member and is preferably a medical device balloon that is inflatable. Suitable expandable members are medical device balloons that expand in response to infusion of a suitable fluid such as saline solution or the like. An example of a suitable material for the expandable member is one that comprises a polyamide material, such as a nylon material.

The dilatation catheter 10 can also include a passageway 22 defined between the outer tubular member 12 and the inner tubular member 14. The passageway 22 can be employed to direct fluid to flow into the expandable member 18 when the expandable member is of the type that is expanded by fluid pressure. The proximal end portion 24 of the outer tubular member 12 and proximal end portion 26 of the inner tubular member 14 (shown in phantom in FIG. 1) are connected to an adapter 28. The adapter 28 includes an access port 30, such as a luer connector, for injecting fluid within the passageway 22 of the dilatation catheter to expand the expandable member 18 when a fluid-expandable member is used. Furthermore, the distal end portion 20 of the outer tubular member 12 is secured to the inner tubular member 14 at 32 to create a fluid tight seal that prevents leakage of fluid from the dilatation catheter 10.

Figure 2:
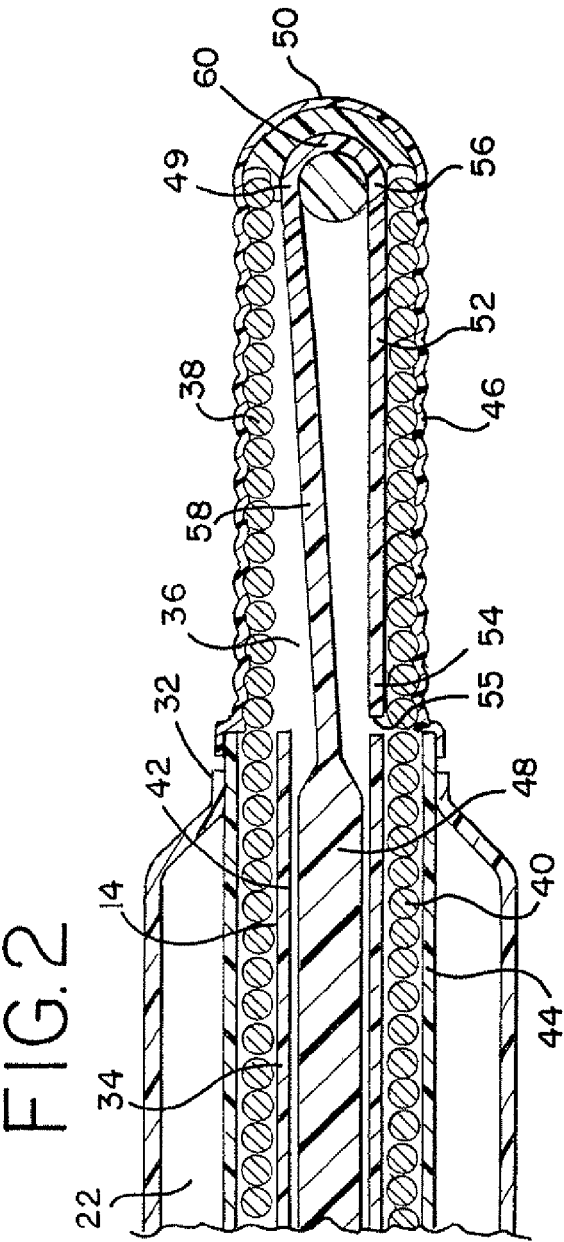
FIG. 2 is an enlarged cross-sectional view of the distal end portion of the fixed wire dilatation catheter of FIG. 1.

The inner tubular member 14 is generally similar to the guidewire disclosed in co-owned U.S. Pat. No. 7,128,718 to Hojeibane et al. and co-owned U.S. Published Patent Application No. 2004/0082881, to Grewe et al., filed Oct. 23, 2003, both of which are hereby incorporated herein by reference. The inner tubular member 14 is comprised of an elongated flexible shaft 34, which can be a hypotube. The distal end portion 38 of the inner tubular member 14, which is also the distal end portion of the dilatation catheter 10, is preferably comprised of a flexible member, such as the illustrated helical coil. The inner tubular member also includes an inner lumen 36 that extends therethrough. Referring to FIG. 2, when the distal end portion 38 of the inner tubular member 14 is comprised of a helical coil, the proximal end portion 40 of the helical coil overlaps the distal end portion 42 of the shaft 34 and the helical coil is bonded, such as by epoxy, to the outer surface of the distal end portion 42 of the shaft 34.

The strand forming the helical coil can have a variety of cross-sectional shapes, such as the illustrated circular shape or a square or rectangular shape, or can be generally flat in cross-section. Typical materials out of which the helical coil could be made include platinum tungsten, with the proximal turns being wound such that adjacent turns are in contact with each other. While the illustrated embodiment of the present invention includes a helical coil, this element may take the form of other types of flexible members, such as metallic tubes with or without portions of the tube removed by, for example laser cutting or bellows folds.

The inner tubular member 14 can include a barrier sheath 44 (FIG. 2), typically made of an elastomeric polymer, that can cover the shaft 34 and the distal end portion 38 of the inner tubular member 14. The barrier sheath 44 prevents fluid injected into the passageway 22 from entering the inner lumen 36 of the inner tubular member 14 and also prevents blood and other fluids from entering into the distal end portion 38 of the inner tubular member 14. The portion 46 of the barrier sheath 44 covering the distal end portion 38 of the inner tubular member 14 preferably conforms to the shape of the distal end portion 38 and is sufficiently elastic to allow the distal end portion 38 of the inner tubular member 14 to deflect and elongate, as will be described in more detail below. The portion of the barrier sheath 44 covering the shaft 34 of the inner tubular member 14 should also be sufficiently elastic to allow the shaft 34 to bend as it is advanced through the vasculature of a patient.

An elongated deflection member 48 extends through the inner lumen 36 of the inner tubular member 14 from the adapter 28 to the distal end portion 38 of the inner tubular member 14. The deflection member 48 has a distal end portion 49 that is connected to an attachment member 50, such as the illustrated rounded epoxy bead, which is disposed at or near the distal tip of the inner tubular member 14. Additionally, the dilatation catheter 10 includes a retaining member 52 located within the inner lumen 36 of the inner tubular member 14. The retaining member 52 has a proximal end portion 54 and a distal end portion 56. The distal end portion 56 of the retaining member 52 is connected to the attachment member 50, and the proximal end portion 54 includes a free end 55 that is slidably movable within the inner lumen 36 and releasably engageable with the inner tubular member 14, as will be explained in more detail below.

Referring to FIG. 2, the elongated deflection member 48 takes the form of a small diameter cylindrical deflection member having an intermediate portion which is reduced in thickness, such as by having been flattened, to form a thin deflection ribbon 58. The distal end 49 of the deflection member 48 typically is further reduced in thickness, such as by being flattened further, and is bent back approximately 180 degrees, possibly slightly greater than 180 degrees, to form a U-shaped bend or portion 60 between the deflection ribbon 58 and the retaining member 52. The U-shaped portion 60 between the deflection ribbon 58 and the retaining member 52 typically is suitably encapsulated by the attachment member 50.

The deflection member 48 and the retaining member 52 can be of unitary construction or can be made up of two discreet elements. As may be appreciated, with a unitary construction of the deflection member 48 and retaining member 52, the ribbon 58 of the deflection member 48 and the retaining member 52 align so that they have a spaced-apart relative orientation, which encompasses having the deflection member ribbon 58 and retaining member 52 vary in spaced-apart positioning with respect to each other, being within respective planes that can be generally parallel or can converge and/or curve with respect to each other, some such positioning being as generally illustrated in the drawings. In addition, the U-shaped bend portion 60 when encapsulated into the rounded bead assists in properly spacing the retaining member 52 and the deflection ribbon 58 with respect to each other.

As illustrated in FIG. 2, if desired, the distal end portion 56 of the retaining member 52 advantageously can be attached to the attachment member 50 at a position offset from the center of the attachment member 50. In addition, if desired, the distal end portion 49 of the deflection member 48 advantageously can be attached to the attachment member 50 at a position offset from the center of the attachment member 60 in an opposite direction from the offset of the retaining member 52.

Referring to FIG. 1, the adapter 28 includes a control member 62 which can be manipulated in accordance with operational characteristics of the control member chosen for this task. This can impart mechanical advantage or operate with movements such as sliding, rotating, bending, pivoting, for example, or other transmission characteristics. Whatever the operational characteristics of the control member 62, the deflection member 48 is moved longitudinally in a proximal or distal direction. More specifically, the control member 62 is coupled to the proximal end portion 64 of the deflection member 48, and movement of the control member 62 causes the distal end portion 38 of the inner tubular member 14 to either elongate in a distal direction (FIG. 3) or deflect away from the longitudinal axis "X" of the inner tubular member 14 in a direction opposite from the location of the retaining member 52 (FIG. 4).

In operation, the dilatation catheter 10 is inserted into and advanced through the vasculature of the patient and is preferably monitored via fluoroscopy. As illustrated in FIG. 2, the distal end portion 38 of the inner tubular member 14 is in a normally linear or straight-line configuration. As the dilatation catheter 10 is advanced through the vasculature, the dilatation catheter can be steered through the tortuous vasculature, such as by a combination of rotating the dilatation catheter and deflecting the distal end portion 38 of the inner tubular member 14.

To deflect the distal end portion 38 of the inner tubular member 14, the control member 62 is manipulated according to its operational characteristics so as to cause the deflection member 48 to move in a proximal direction. Referring to FIG. 4, as the deflection member 48 is moved in the proximal direction, the retaining member 52 initially also moves proximally so that the proximal end portion 54 of the retaining member 52 engages a component of the device, such as the inner tubular member 14.

Typically and more particularly, when the distal end portion 38 of the inner tubular member 14 is comprised of coils which overlap the shaft 34 of the inner tubular member 14, the proximal end portion 54 of the retaining member 52 engages a location on the inside of the device, typically the inner tubular member 14, in a manner to secure the free end 55 so it does not move appreciably in the proximal direction. For example, the free end 55 can abut the distal end portion 42 of the shaft 34, possibly becoming inserted or wedged between the overlapped portion of the shaft 34 and the coils of the helical distal end portion 38. By thus preventing any further proximal movement of the retaining member 52, this member changes from a slidably movable mode to an engaged mode, typically being a releasably engageable mode.

The engagement between the retaining member 52 and the inner tubular member 14 results in the lower portion of the attachment member 50 remaining at a fixed distance from the distal end portion 42 of the shaft 34 of the inner tubular member. As the deflection member 48 is moved further in the proximal direction, the deflection ribbon 58 will be pulled in a direction away from the retaining member 52. The movement of the deflection ribbon 58 in a direction away from the retaining member 52 causes the distal end portion 38 of the inner tubular member 14 to deflect away from the longitudinal axis "X" of the inner tubular member 14 in a direction opposite that of the retaining member 52.

In this embodiment, the distal end portion 38 of the inner tubular member 14 only deflects in one direction. Therefore, to steer the dilatation catheter 10 through the vasculature of a patient, the dilatation catheter must also be rotated to orient the distal end portion 38 of the inner tubular member 14 in the desired direction. For example, if the dilatation catheter 10 is oriented so that the distal end portion 38 of the inner tubular member 14 can be deflected in an upward direction, but the dilatation catheter 10 needs to be maneuvered into a downward direction, the dilatation catheter can be rotated 180 degrees so that the distal end portion 38 is deflected in a downward direction.

Once the distal end portion 38 of the inner tubular member 14 is positioned at the site of a occlusive vascular disease, the expandable member 18 is expanded. When the expandable member 18 is an inflatable balloon, fluid is injected through the access port 30 and into passageway 22 to inflate the balloon. The expandable member 18 is expanded to center the distal end portion 38 of the inner tubular member 14 with respect to the blood vessel and the occlusive vascular diseased site. After the distal end portion 38 is centered, it can be extended or elongated by manipulating the control member 62 in accordance with its operational characteristics in order to move the deflection member 48 in a distal direction. Referring to FIG. 3, movement of the deflection member 48 in the distal direction causes the distal end portion 38 of the inner tubular member 14 to extend or distally elongate in a substantially axial direction. When the distal end portion 38 of the inner tubular member 14 is comprised of a helical coil, the coils separate from each other as the distal end portion is elongated.

Depending on the size, shape and hardness of the vascular disease lesion, the elongation of the distal end portion 38 can be used in various different manners to treat the occlusive vascular diseased site. For example, when the diseased site is relatively soft and/or relatively short in length, the distal end portion 38 of the inner tubular member 14 can be elongated or extended to advance the distal end portion through the lesion or diseased site. Alternatively, when the diseased site is relative hard, the distal end portion 38 of the inner tubular member can be used for a dottering procedure to achieve a pecking- or drill-like action to loosen and/or break through the lesion or diseased site. The dottering action of the distal end portion 38 can be generated by repeatedly manipulating the control member to impart differently direct impetus to the deflection member 48. For example, for a longitudinally operating control member 62, moving its housing in a back and forth action causes the distal end portion 38 to extend and retract to achieve the desired dottering action. Furthermore, the distal end portion 38 also can be elongated or extended to initially engage the lesion or diseased site, for example, to form an initial pathway into the lesion or diseased site. The expandable member 18 could then be unexpanded or deflated and the entire dilatation catheter 10 could be advanced distally to complete the formation of the pathway through the occlusive vascular diseased site.

As will be appreciated, the expandable member 18 can be used to center or position the distal end portion 38 of the inner tubular member 14 prior to contacting the lesion or diseased site. The centering of the distal end portion 38 assists in reducing the risk of the distal end portion becoming misaligned, and thus reduces the risk of perforating the vessel. Additionally, the expandable member 18 can be used to dilate the blood vessel to relieve some of the pressure compressing the lesion or diseased site, which can aid in the advancement of the distal end portion 38 therethrough.

After the dilatation catheter 10 has formed a passageway through the lesion or diseased site, the dilatation catheter is withdrawn from the vasculature of the patient.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A steerable dilatation catheter having an elongated axis and a closed distal end portion, the catheter comprising:
    an outer flexible tubular member having an expandable member near the distal end thereof;
    an inner flexible tubular member disposed within the outer flexible tubular member, said inner flexible tubular member having a proximal end portion, a distal end portion and a lumen disposed therein, the distal end portion of the inner flexible tubular member operatively engaging the closed distal end portion of the catheter;
    the inner flexible tubular member further includes a shaft that has a distal end portion located proximal of the closed distal end portion of the catheter;
    said distal end portion of the inner flexible tubular member extends distally beyond the distal end of the outer flexible tubular member, and said distal end of the outer flexible tubular member is secured to the inner flexible tubular member;
    an elongated deflection member slidably disposed within the lumen of the inner flexible tubular member, said deflection member having a proximal end portion and a distal end portion, the distal end portion of the deflection member being operatively connected to the closed distal end portion of the catheter;
    a retaining member having a proximal end portion and a distal end portion, the distal end portion of the retaining member is operatively connected to the closed distal end portion of the catheter, and the proximal end portion of the retaining member includes a free end that is the proximal end of the retaining member, said retaining member terminates at said proximal free end, said retaining member being slidably movable within the lumen of the inner flexible tubular member and releasably engageable with the shaft distal end portion when the elongated deflection member moves proximally;
    movement of the elongated deflection member distally causes the distal end portion of the inner tubular member to elongate in a substantially axial direction generally along the axis of the catheter; and
    movement of the elongated deflection member proximally results in the proximal free end of the retaining member releasably engaging the shaft distal end portion of the inner tubular member causing the distal end portion of the inner tubular member and the closed distal end portion of the catheter to deflect from the axis of the catheter.

2. The dilation catheter of claim 1, wherein the expandable member is an inflatable balloon.

3. The dilatation catheter of claim 2, wherein a passageway is located between the outer tubular member and the inner tubular member, said passageway being in fluid communication with the inflatable balloon and adapted to communicate fluid to the inflatable balloon.

4. The dilatation catheter of claim 3, wherein a barrier sheath covers the inner tubular member to prevent fluid from entering the lumen of the inner tubular member.

5. The dilatation catheter of claim 1, wherein the distal end portion of the inner tubular member includes a helical coil.

6. The dilatation catheter of claim 1, further including a control member in operative engagement with said proximal end portion of the elongated deflection member, said control member effecting said movement of the deflection member distally.

7. The dilatation catheter of claim 1, further including a control member in operative engagement with said proximal end portion of the elongated deflection member, said control member effecting said movement of the deflection member distally and said movement of the deflection member proximally.

8. A steerable dilatation catheter having an elongated axis and a closed distal end portion, the catheter being for treating occlusive vascular disease within the vasculature of a patient, comprising:
an elongated member having a deflectable distal end portion extending to the closed distal end portion of the catheter for guiding the elongated member through the vasculature of a patient to a site of occlusive vascular disease;
a deflection member slidably positioned within said elongated member, and a retaining member connected to the closed distal end portion of the catheter; the retaining member has a free end that is the proximal end of the retaining member, said retaining member terminates at said proximal free end, said proximal free end being slidably moveable within the elongated member and removably engageable with the distal end portion of the elongated member, wherein distally directed movement of the deflection member causes the distal end portion of the elongated member to extend, and proximally directed movement of the deflection member causes the proximal free end of the retaining member to releasably engage an engagement portion of the elongated member, the engagement portion being proximal of the proximal free end of the retaining member, causing the distal end portion of the elongated member and the closed distal end portion of the catheter to deflect from the axis of the catheter;
a control member in operative engagement with said elongated member, said control member being operative to repeatedly distally extend and proximally retract said deflectable distal end portion of the elongated member in a substantially axial direction through a length of the distal end portion of the elongated member, which length is as long as at least the entire length of the retaining member, and which length extends said distal end portion into the occlusive vascular disease site, whereby the catheter treats the occlusive vascular disease site by a dottering procedure; and
an expandable member located along the elongated member at a location proximal of the distal end portion.

9. The steerable dilatation catheter of claim 8, wherein the elongated member comprises an outer tubular member having an inner tubular member disposed therein.

10. The steerable dilatation catheter of claim 8, wherein the expandable member is an inflatable balloon.

11. The steerable dilatation catheter of claim 8, wherein the distal end portion of the elongated member comprises a helical coil.

12. A steerable dilatation catheter having an elongated axis and a closed distal end portion, comprising:
an outer flexible tubular member (12) having an inflatable balloon (16) near the distal end thereof;
an inner flexible tubular member (14) having an inner lumen, said inner flexible tubular member disposed within the outer flexible tubular member, said inner flexible tubular member having a proximal end portion and a distal end portion including a flexible helical coil, the distal end portion of the inner flexible tubular member extends to the closed distal end portion of the catheter;
said distal end portion of the inner flexible tubular member extending distally beyond the distal end of the outer flexible tubular member, and said distal end of the outer flexible tubular member being secured to the inner flexible tubular member;
a passageway defined between the outer tubular member and the inner tubular member, said passageway being in fluid communication with the inflatable balloon;
an elongated deflection member being slidably disposed within said inner lumen of the inner tubular member, said elongated deflection member having a proximal end portion and a distal end portion, the distal end portion of the elongated deflection member being operatively connected to the closed distal end portion of the catheter;
a retaining member having a proximal end portion and a distal end portion, the distal end portion of the retaining member is operatively connected to the closed distal end portion of the catheter, and the proximal end portion of the retaining member includes a free end that is the proximal end of the retaining member, said retaining member terminates at said proximal free end, said proximal free end being slidably movable within the inner lumen of the inner flexible tubular member;
the inner flexible tubular member further includes a shaft that has a distal end portion located proximal of the closed distal end portion of the catheter, the retaining member proximal free end being adapted to releasably engage the shaft distal end portion when the elongated deflection member is moved in a proximal direction; and
movement of the elongated deflection member distally causes the distal end portion of the inner tubular member to elongate in a substantially axial direction generally along the axis of the catheter, and movement of the elongated deflection member proximally results in the proximal free end of the retaining member releasably engaging the shaft distal end portion causing same and the closed distal end portion of the catheter to deflect from the axis of the catheter.

13. A method of treating occlusive vascular disease of a blood vessel, comprising:
providing a steerable dilatation catheter having an elongated member with an expandable member positioned along the elongated member and with an extendable distal end portion distally positioned with respect to the expandable member and a retaining member connected to the extendable distal end portion, and a control member in operative engagement with the elongated member;
further providing the retaining member of the steerable dilation catheter to have a free end at its proximal end, providing this proximal free end at a location distal of an engagement portion of the elongated member and within the elongated member;
advancing the extendable distal end portion of the elongated member through the vasculature of a patient to an occlusive vascular disease site;
manipulating the control member to thereby distally extend and proximally retract the extendable distal end portion of the elongated member in a substantially axial direction through a length thereof that is as long as at least the entire length of the retaining member and thereby engage and thus treat the occlusive vascular disease site through a dottering procedure by repeatedly extending and retracting the deflectable distal end portion of the elongated member thereby repeatedly contacting the vascular disease site with the distal end portion of the elongated member; and manipulating the control member to thereby proximally move the retaining member proximal free end into removeable engagement with the engagement portion of the elongated member causing the extendable distal end portion of the elongated member to deflect from its axis.

14. The method of claim 13, further including centering the distal end portion of the elongated member prior to treating the occlusive vascular disease site.

15. The method of claim 14, further including axially enlarging the expandable member in order to center the distal end portion of the elongated member.

16. The method of claim 13, wherein treating the occlusion vascular disease site includes extending the distal end portion of the elongated member through the occlusion vascular disease site.

17. The method of claim 13, wherein treating the occlusive vascular disease site includes initiating a pathway through the site with the distal end portion of the elongated member.

18. The method of claim 13, further including dilating the vasculature prior to or during the extending of the distal end portion of the elongated member.

* * * * *